United States Patent
Pflueger

(10) Patent No.: US 7,758,489 B2
(45) Date of Patent: *Jul. 20, 2010

(54) SPINAL DISC THERAPY SYSTEM

(76) Inventor: D. Russell Pflueger, 26911 Windsor Dr., San Juan Capistrano, CA (US) 92675

( * ) Notice: Subject to any disclaimer, the term of this patent is extended or adjusted under 35 U.S.C. 154(b) by 191 days.

This patent is subject to a terminal disclaimer.

(21) Appl. No.: 11/787,046

(22) Filed: Apr. 13, 2007

(65) Prior Publication Data

US 2007/0197853 A1    Aug. 23, 2007

Related U.S. Application Data

(63) Continuation of application No. 10/437,273, filed on May 13, 2003, now Pat. No. 7,223,227.

(60) Provisional application No. 60/379,877, filed on May 13, 2002.

(51) Int. Cl.
*A61N 2/00* (2006.01)
(52) U.S. Cl. ...................................... 600/12; 623/17.16
(58) Field of Classification Search ............... 600/1–15; 623/17.12, 17.16, 23.62; 606/32, 96.01, 606/104, 97.01, 103.05, 915, 921, 35, 41; 424/423–426; 604/890.1, 891.1
See application file for complete search history.

(56) References Cited

U.S. PATENT DOCUMENTS

| 4,393,041 | A | 7/1983 | Brown et al. |
|---|---|---|---|
| 4,772,287 | A | 9/1988 | Ray et al. |
| 4,904,260 | A | 2/1990 | Ray et al. |
| 5,139,527 | A | 8/1992 | Redl et al. |
| 5,869,080 | A | 2/1999 | McGregor et al. |
| 6,013,853 | A | 1/2000 | Athanasiou et al. |
| 6,187,048 | B1 | 2/2001 | Milner et al. |
| 6,454,804 | B1 | 9/2002 | Ferree |
| 6,500,173 | B2 | 12/2002 | Underwood et al. |
| 6,558,390 | B2 | 5/2003 | Cragg |

*Primary Examiner*—John P Lacyk
(74) *Attorney, Agent, or Firm*—Stout, Uxa, Buyan & Mullins, LLP; Frank J. Uxa

(57) ABSTRACT

Spinal disc therapy systems in accordance with the present invention generally include an implant element structured to have a therapeutic effect on a human or animal body when implanted into an intervertebral disc annulus or intervertebral disc nucleus. The implant element may include a biochemically active agent that provides pain relief, inflammation relief or other benefit to the human or animal body. The implant element may be mechanically active or mechanically activatable in being effective in providing a therapeutic effect to the human or animal body when implanted in the intervertebral disc. For example, the implant element may include a mechanically active or mechanically activatable component that radiates wave energy, for example, in the form of electrical or magnetic energy, into the body.

17 Claims, 2 Drawing Sheets

SPINAL DISC THERAPY SYSTEM

RELATED APPLICATIONS

This is a continuation of U.S. patent application Ser. No. 10/437,273 filed on May 13, 2003, which application claims the benefit of U.S. provisional application No. 60/379,877 filed on May 13, 2002, the entire disclosures of which are incorporated herein by this specific reference.

BACKGROUND OF THE INVENTION

The medical industry is constantly evolving through the discovery and development of new pharmaceutical, biotechnology, and medical device products and procedures. Techniques and technologies are being developed to treat internal areas of the body through less invasive means.

Recently, devices have been developed to explore and therapeutically impact areas inside the spinal canal. These devices are primarily designed to reduce the amount of pain that chronic pain patients are experiencing due to abnormal conditions existing in and around the spinal cord and intervertebral discs. Procedures and devices currently used to treat these areas include: spinal injections of anesthetics and anti-inflammatories, RF and cryo neuroablation, epiduroscopes, infusion catheters, spinal stimulation devices, micro endoscopic discectomy instruments, and the like.

The spinal column includes, among other structures, the bony vertebrae which surround the spinal cord, and the intervertebral discs. In a healthy spine, the discs maintain separation between the vertebrae, promote fluid circulation throughout the spine, and provide a cushioning effect between the bony vertebral structures.

Due to the elastic nature of an intervertebral disc, the disc is subject to injury if the disc becomes overstressed, for example, by trauma to the spine, excess body weight, improper mechanical movements and the like. Intervertebral disc injuries and other abnormalities result in serious back pain and physical disability and are often chronic and difficult to treat. Such abnormalities include, but are not limited to, localized tears or fissures in the disc annulus, localized disc herniations with contained or escaped nuclear extrusions, and circumferential bulging discs. Discs also experience degeneration over time which can accelerate these problems.

Disc fissures may result from structural degeneration of fibrous components of the disc annulus (annulus fibrosis). More specifically, fibrous components of the annulus become separated in particular areas, creating a fissure within the annulus. Sometimes the fissure is accompanied by extrusion of material from the disc nucleus (nucleus pulposus) into the fissure. Biochemicals may escape from the disc and irritate surrounding structures. These disc fissures are known to be extremely painful. The fissure may also be associated with herniation of that portion of the annulus wall.

With a contained disc herniation, the nucleus pulposus may work its way partly through the annulus. The outward protrusion of fibrous and nuclear material can press upon the spinal nerves or irritate other body structures.

Another common disc problem occurs when the entire disc bulges circumferentially about the annulus rather than in specific, isolated locations. This may occur for example, when over time, the disc weakens, bulges, and takes on a "roll" shape. The joint may become unstable and one vertebrae may eventually settle on top of another. This problem typically continues to escalate as the body ages, and accounts for shortened stature in old age. Osteophytes may form on the outer surface of the disc and further encroach upon the spinal canal and nerve foramina. This condition is called spondylosis.

Traditional non-surgical treatments of disc degeneration and abnormalities include bed rest, pain and muscle relaxant medication, physical therapy or steroid injection. Such therapies are directed primarily at pain relief and delaying further disc degeneration. In many cases, non-surgical approaches fail and surgical methods of treatment may be applied. Spinal fusion methods are aimed at causing the vertebrae above and below the injured disc to grow solidly together forming a single piece of bone. This procedure is carried out with or without discectomy (surgical removal of the disc). Another procedure, endoscopic discectomy, involves removing tissue from the disc percutaneously in order to reduce the volume of the disc, thereby reducing impingement of the surface of the disc on nearby nerves.

Endoscopic Discectomy is an outpatient surgical procedure to remove herniated disc material. Using local anesthesia with the help of x-ray video image for guidance, an endoscopic probe is inserted between the vertebrae and into the herniated disc space through the skin of the back. Surgical attachments (cutters, lasers, and the like) are then sent down the hollow center of the probe to remove a portion of the offending disc. Sometimes, the surgical attachments can be used to push the bulging disc back into place and for the removal of disc fragments and small bone spurs. This form of discectomy utilizes the same tools used for knee surgery but maneuvers the instruments above the spine. The surgeon introduces the endoscope through a large, approximately 10 mm or greater, incision into the skin above the spine, then locates the nerve and disc using direct visualization. This surgery can be done through the abdomen for anterior discectomy as well. These procedures are performed under direct endoscopic visualization which increases the incisional space requirement and may require a hemi-laminectomy (surgical removal of part of the lamina).

Ray et al, U.S. Pat. No. 4,904,260 and Ray et al, U.S. Pat. No. 4,772,287, the disclosure of each of which is incorporated herein in its entirety by this specific reference, disclose a pair of prosthetic intervertebral disc capsules alleged to be useful for maintaining height and motion to a human spine and imitating the natural rheology of intradiscal nuclear material.

Feree, U.S. Pat. No. 6,454,804 B1, incorporated herein in its entirety by this specific reference, discloses a technique for adding engineered annulus fibrosis cells onto a surface of a diseased or damaged intervertebral disc annulus.

There continues to be a need for systems for safely and effectively treating at least one of pain, inflammation, nutrient deficiency, hormonal imbalance, other disorders and conditions, and the like in a human or animal having an intervertebral disc.

SUMMARY OF THE INVENTION

The present invention generally comprises spinal disc therapy systems for treatment of one or more of pain, inflammation, nutrient deficiency, hormonal imbalance, other disorders and conditions and the like in a human or animal having an intervertebral disc. Methods of using such systems are included without the scope of the present invention. The present systems are relatively straightforwardly structured and can be placed or implanted in the intervertebral disc relatively easily and, preferably, substantially minimally invasively. The present systems advantageously are effective in treating the condition and/or disorder on a substantially continuous, relatively long term basis. Thus, the present systems and methods are particularly effective and useful in treating chronic conditions and/or disorders. In any event, the present systems and methods are effective in providing useful benefits to the human or animal.

In a broad aspect of the present invention, systems are provided which generally comprise an implant element structured to be placed, introduced, or implanted into an intervertebral disc of a human or animal.

Advantageously, the implant element comprises a therapeutic component effective in treating a condition (meaning to include a condition or disorder desired to be treated and/or in need of treatment) in the human or animal in whom the implant element is placed or located. For example, in some embodiments of the invention, the implant element comprises a mechanically active, and/or mechanically activatable, therapeutic component. Preferably, such a therapeutic component provides at least one of a magnetic field, an electrical field, a radioactive field and the like and combinations thereof, for example, in, or in proximity to, the intervertebral disc in which the implant element is placed or located. In one embodiment, the therapeutic component may comprise one or more of a magnetic component, an electrode element, and/or a radioactive material.

In a useful embodiment of the invention, the therapeutic component is structured to be remotely activatable from a source external to the intervertebral disc in which the implant element is placed or located. For example, the implant element may be structured to be effective in providing electrical energy to at least one of the intervertebral disc and a region of the body in proximity to the intervertebral disc. For example, the therapeutic component may comprise at least one electrode, for example, a pair of electrodes, that are activatable to deliver electrical energy to the intervertebral disc or a region in proximity to the intervertebral disc, by means of or using a device, for example a controller, located outside of or remote to the intervertebral disc.

In one useful embodiment of the invention, the implant element comprises a biochemically active component, for example, a chemical agent, a medicinal agent, an anaesthetic, a nutrient supplement, or other suitable pharmaceutical agent and the like and mixtures thereof, that provides a benefit to the body in which the implant element is placed or located. The biochemically active component is provided in an amount effective in treating a condition in the body, for example, but not limited to, a condition, such as pain, existing in or emanating from a region encompassing the intervertebral disc in which the implant element is placed.

The implant element is structured to be implantable into the nucleus of a disc, for example, aligned along an inner wall of the annulus. Alternatively, the implant element is structured to be implantable into the annulus, for example, between the fibrous lamellae. The implant element may be in the form of, for example, but not limited to, a solid pellet, a fluid filled capsule, or a gelatinous ribbon or strand. In some embodiments of the invention, the implant element is specifically structured to be implantable, for example, by being directly injected into a portion of the annulus of an intervertebral disc, for example, such that the implant element is positioned between the fibrous lamellae.

Advantageously, the present systems may further comprise a delivery device, structured to contain the implant element and structured to deliver the implant element to the intervertebral disc. For example, the delivery device may be structured to enable delivery of the implant element to the disc based on a specific need of the patient. The delivery device may be structured to enable adjustable sizing or portioning of the implant element to be delivered to the intervertebral disc.

In a particularly useful embodiment, the implant element of the present systems is structured to allow or provide for release of the therapeutic component into the intervertebral disc in a time controlled manner, for example, at least one of a delayed release manner, a sustained release manner and an otherwise controlled release manner. Such embodiment is advantageously useful in the treatment of chronic conditions.

In one embodiment of the invention, the implant element comprises a biochemically active component and an excipient component or a non-therapeutic component, for example, an excipient component comprising a biochemically inactive, or substantially biochemically inactive, component. The excipient or non-therapeutic component, for example, may comprise an effective amount of an encapsulating material, a complexing component, a coating material, a filler material, a matrix material and combinations thereof. The implant element may comprise a biochemically active agent incorporated with or enclosed within a bioabsorbable, chemically inert material that allows a delayed, sustained and/or otherwise controlled release of the biochemically active or pharmaceutical component into the intervertebral disc in which the implant element is placed or located.

Suitable such non-therapeutic or excipient components are known in the art. Such components should be selected to be effective in the present invention, for example, to provide for time controlled release of the therapeutic component. In addition, such non-therapeutic components should have no substantial or significant detrimental effect on the intervertebral disc and the human or animal in whom the implant element is placed or located.

In a very useful embodiment, the biochemically active component is combined with a cyclodetrin. Without wishing to limit the invention to any particular theory or mechanism of operation, it is believed that the combination of biochemically active component and cyclodextrin forms complexes, for example, inclusion complexes. Over time, the biochemically active component is released from such complexes and is available to provide the desired therapeutic effect.

In some embodiments of the invention, the implant element is structured to be placed into a nucleus of the intervertebral disc. Alternatively or additionally, the implant element is structured to be placed into a disc annulus, for example, between adjacent fibrous components, or lamellae, that make up the annulus.

The present invention additionally provides methods for treating a condition in a human or animal having an intervertebral disc. More particularly, methods in accordance with the present invention generally comprise the steps of placing an implant element into an intervertebral disc, for example, into a nucleus or an annulus of an intervertebral disc, and, preferably, thereafter allowing or causing the implant element to provide a therapeutic effect to the disc or to a region in proximity to the disc. Preferably, the implant element includes a therapeutic component effective in treating a condition, for example, effective in reducing at least one of inflammation, pain, such as pain emanating in or in proximity to an intervertebral disc in which the implant element has been placed, nutrient deficiency, hormonal imbalance and other conditions that can be treated with the methods of the present invention.

It is noted that the spinal disc therapy systems in accordance with the present invention and described elsewhere herein are especially suitable for use in the methods of the present invention.

For example, in some embodiments of the methods of the invention, the implant element comprises a biochemically active component, and an excipient component, as described elsewhere herein. In addition, the method may include the step of allowing at least a portion of the implant element to be substantially assimilated into or absorbed by the body of the human or animal, for example, the intervertebral disc in which the implant element has been placed. In some embodiments of the methods of the present invention, the implant element is allowed to be substantially entirely absorbed into the body of the human or animal being treated.

In other embodiments of the methods of the invention, the implant element comprises a mechanically active, or mechanically activatable, therapeutic component, as described elsewhere herein. In these embodiments of the invention, the methods may further comprise the step of providing, for example, radiating, wave energy from the implant element into the body of the human or animal in which the implant element is located. The method may additionally include the step of activating, for example, remotely activating, the therapeutic component of the implant element in order to cause a therapeutic effect on the body of the human or animal, for example, the intervertebral disc or a region in proximity to the intervertebral disc, in which the implant element has been placed.

Any and all features described herein and combinations of such features are included within the scope of the present invention provided that the features of any such combination are not mutually inconsistent.

These and other aspects of the present invention are apparent in the following detailed description and claims, particularly when considered in conjunction with the accompanying drawings in which like parts bear like reference numerals.

BRIEF DESCRIPTION OF THE DRAWINGS

FIG. 4 shows a simplified diagram of an intervertebral disc being treated with the spinal disc therapy system in accordance with the present invention, the system comprising an implant element structured to be placed into a disc annulus of an intervertebral disc.

FIG. 4a shows another simplified diagram of an intervertebral disc being treated with the spinal disc therapy system in accordance with the present invention, the system comprising an implant element structured to be injected as a gelatinous material into a disc annulus of an intervertebral disc.

DETAILED DESCRIPTION

Figure 1:
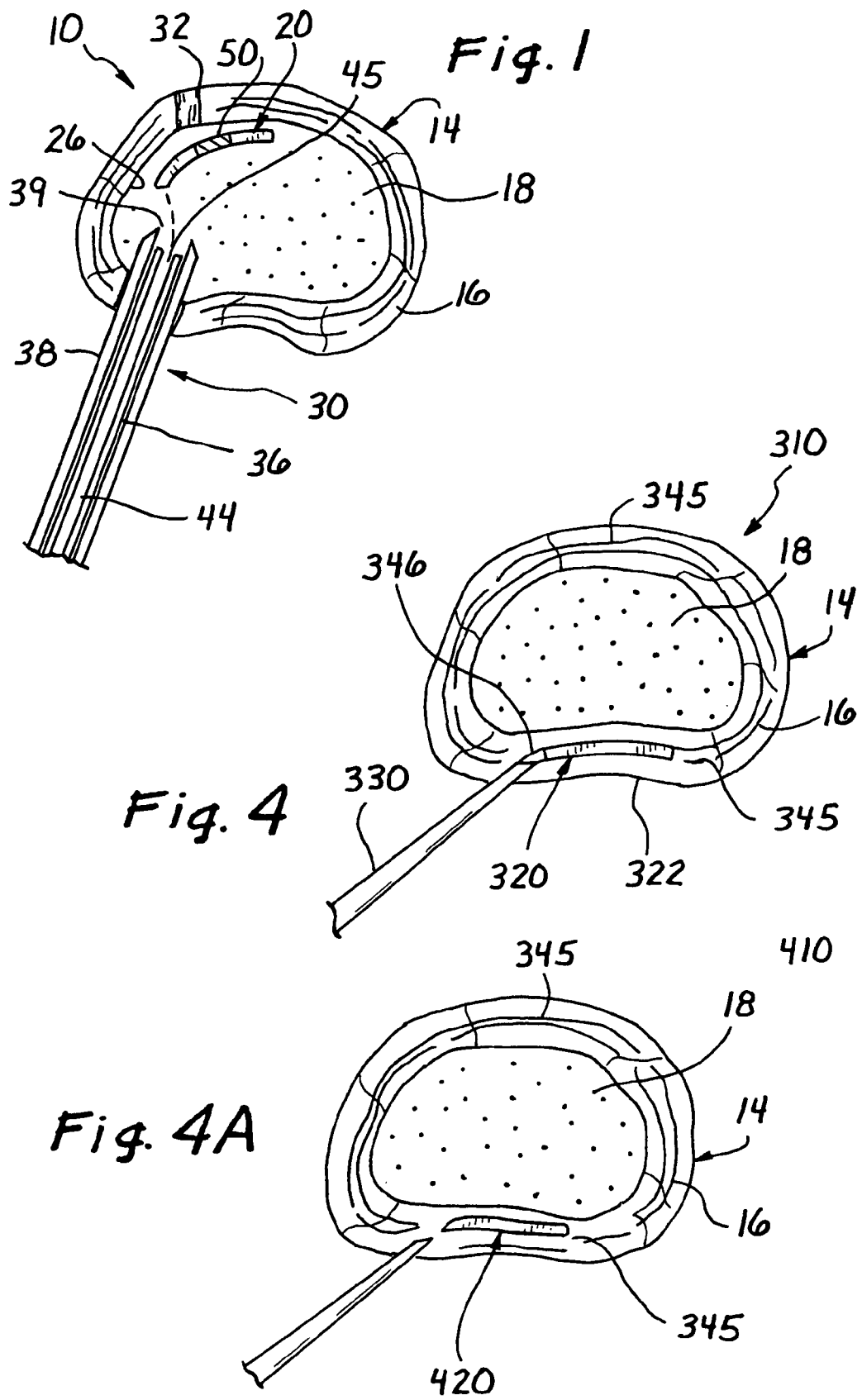
FIG. 1 shows a simplified diagram of an intervertebral disc being treated with a spinal disc therapy system in accordance with the present invention, the system comprising an implant element structured to be placed within a nucleus of the intervertebral disc.

Turning now to FIG. 1, a spinal disc therapy system, in accordance with the present invention, is shown generally at 10 and is shown located in an intervertebral disc 14 of a human or animal patient.

Generally, the intervertebral disc 14 includes an outer ligamentous ring, or annulus fibrosis, (hereinafter referred to as the "annulus 16"), and an inner nucleus pulposus (hereinafter referred to as the "nucleus 18").

The annulus 16 of an intervertebral disc 14 is comprised of cells (fibrocyte-like and chondrocyte-like), collagen fibers and non-fibrillar extracellular matrix. The components of the annulus 16 are arranged in about 15 to about 25 lamellae around the nucleus 18. The fibers in the lamellae alternate their direction of orientation by about 30 degrees for each band.

Preferably, the system 10 in accordance with the invention comprises an implant element 20 sized and structured to be placed in the intervertebral disc 14, for example, within the disc nucleus 18, such as with a longitudinal axis of the implant 20 aligned along an inner wall 26 of the disc annulus 16 as shown in FIG. 1.

Once implanted, the implant element 20 is effective, preferably over an extended period of time, such as at least about 1 day or about 1 week to about 1 month or about 1 year or longer, in treating a condition in the body of the human or animal, for example, but not limited to, pain emanating from a nerve, for example, a nerve root, located in, or in proximity to, the intervertebral disc in which the implant element 20 is located. Other conditions that the implant element 20 may be structured to treat include, for example, and without limitation, swelling, inflammation, nutrient deficiencies, hormonal imbalance, and the like and combinations thereof. The implant element 20 may be effective alone, or in combination with one or more additional implant elements in the same intervertebral disc or other intervertebral discs of a human or animal.

As shown in FIG. 1, the implant element 20 may be inserted, or introduced, into the disc 14 by means of a delivery device 30 structured to deliver the implant element 20, or at least a portion thereof, into the intervertebral disc nucleus 18, for example, generally aligned along the inner wall of the annulus 16. In the event the system 10 is being used to treat a torn or damaged annulus, the implant element 20 is preferably aligned adjacent an annulus fissure 32.

Preferably, the delivery device 30 is structured to percutaneously deliver the implant element 20 into the disc nucleus 18. For example, the delivery device 30 may comprise a catheter 36 sized and structured to contain the implant element 20. The catheter 36 may have an inner diameter of between about 0.1 mm to about 7 mm, and more preferably an inner diameter of about 0.5 mm to about 2 mm.

Implantation of the implant element 20 may be facilitated by means of a rigid stylette 38 or other suitable mechanism conventionally used in the art of spinal surgery for accessing interior portions of the spine.

Advantageously, the stylette/catheter arrangement shown in FIG. 1 is effective in providing substantially minimally invasive, direct access to the intervertebral disc nucleus 18. The stylette 38 preferably includes a sharp distal tip 39 that is effective in puncturing and penetrating the skin, underlying muscle tissue and the intervertebral disc annulus 16. The stylette 38 may be structured to provide access to the disc nucleus 18 directly, for example, without the initial provision of a surgical incision. Once the stylette 38 has been satisfactorily placed within the disc 14, the catheter 36 containing the implant element 20 may then be inserted through the stylette 38. At least a portion of the implant element 20 is introduced into the disc 14.

The delivery device 30 preferably includes a mechanism for forcing the implant element 20 out of the catheter 36 and into the disc 14, such as into the disc nucleus 18. For example, the mechanism may comprise a relatively flexible inner element 44, such as a wire, slidably disposed within the catheter lumen, having a distal end 45 structured to be engagable to the implant element 20. After implantation, the implant element 20 can be disengaged from the inner element 44, for example, when the catheter 36 is withdrawn from the nucleus 18.

The implant element 20 may comprise a mechanically active (mechanically activated), and/or mechanically activatable, therapeutic component 50, for example, a component that provides, or can be activated to provide at least one of a magnetic field, an electrical field, an ultrasonic field, radio waves, a radioactive field and the like and combinations thereof in, or in proximity to, the intervertebral disc 14 in which the implant element 20 is located. For example, the therapeutic component may comprise a magnetic component, an electrode element, and/or a radioactive material that radiates a beneficial form of wave energy into the human or animal body.

The therapeutic component 50 may be structured to produce fields of energy having utility in the treatment of pain emanating from nerves located in proximity to the disc 14 by reducing or even eliminating pain signals from nerves located in the field. For example, the therapeutic component 50 may be structured to heat tissues using electrical energy, or destroy diseased cells using radioactive energy. Other uses of electrical, magnetic, radioactive and other waveform energies are contemplated, and will be apparent to those of skill in the art, and are each considered to be included within the scope of the present invention.

Figure 2:
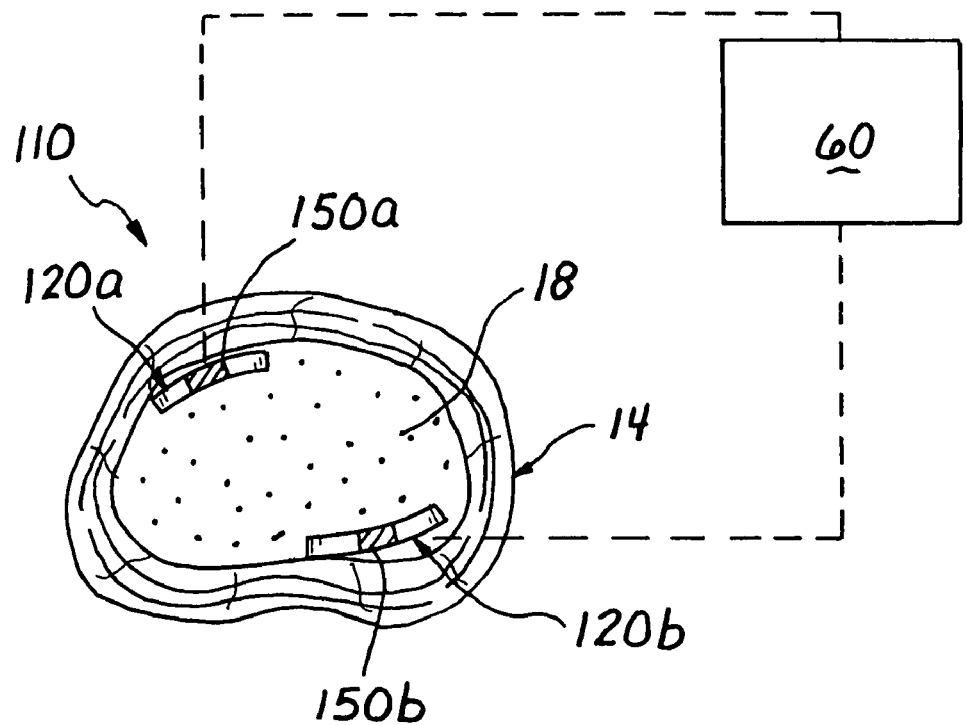
FIG. 2 shows a simplified diagram of an intervertebral disc being treated with an embodiment of the invention, similar to the embodiment shown in FIG. 1, the system further comprising a remote activation device.

Turning now to FIG. 2, another embodiment of the invention is shown generally at 110, this embodiment being similar to the embodiment 10 of the invention shown in FIG. 1, with like elements having like reference numerals increased by 100.

More particularly, FIG. 2 shows a spinal disc therapy system 110 comprising an implant element 120a comprising a remotely activatable therapeutic component 150a, for example, an electrode. The system 110 includes a remote element, for example, a control unit 60, that is structured to enable activation, for example, electrical activation, of the therapeutic component 150a from outside the intervertebral disc 14, for example, from a position external to the patient being treated.

The control unit 60 may be structured to supply an electrical waveform having selected parameters, depending on the therapy to be provided.

FIG. 2 shows another implant element 120b including a therapeutic component 150b, for example, a second electrode connected to the control unit 60. It should be understood therefore, that a plurality of electrodes may be connected to a single control unit, as called for or needed to achieve the desired treatment.

Dashed lines in FIG. 2 are used to indicate that the activatable therapeutic components 150a and 150b are not necessarily "hard-wired" to the control unit 60, but alternatively, may be connected only through energy wave forms, such as magnetic and/or electrical fields.

Figure 3:
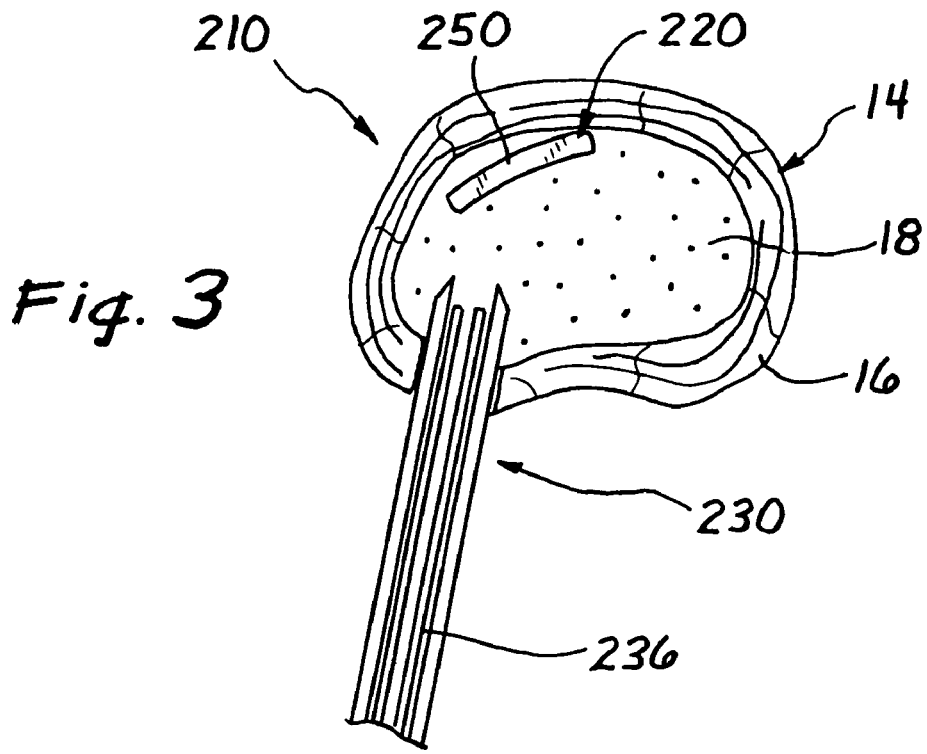
FIG. 3 shows a simplified diagram of an intervertebral disc being treated with another embodiment of a spinal disc therapy system of the present invention, the system including a plurality of implant elements.

Turning now to FIG. 3, another spinal disc therapy system in accordance with the present invention is shown generally at 210. The system 210 is substantially similar to systems 10 and 110 shown in FIGS. 1 and 2, with like elements having like reference numerals increased by 200 and 100, respectively.

The primary difference between system 210 and systems 10 and 110 is that the implant element 220 comprises a therapeutic component 250 including a biochemically active component, for example, an effective amount of a biochemically active component suitable for treating a condition in the patient. The biochemically active component may comprise, for example, a medicinal or pharmaceutical agent, an anti-inflammatory medicine, an anti-pain medicine, an anesthetic agent, a nutritional supplement, a hormonal substance, an analgesic agent and the like and mixtures thereof, depending upon the desired treatment objectives.

Preferably, the implant element 220 further comprises an excipient component, for example, an inactive or substantially inactive component effective to cause time controlled release, for example, delayed, sustained, and/or other controlled release, of the biochemically active component agent into the body of the human or animal, for example, into the disc 14 and/or surrounding structures, in which the implant element 220 is located. The excipient component may be any one or more of the many well known, biologically tolerated, generally inert materials that are useful for providing delayed, sustained and/or other time controlled release of a pharmaceutical or other biochemically active substance into a living body.

For example, the biologically active component of therapeutic component 250 may be encased within a biodegradable or bioabsorbable coating, for example, a coating comprising biodegradable or bioabsorbable polymeric material or other suitable coating substance. Alternatively, the biochemically active component may be encapsulated within a suitable semi-porous, permeable, membrane or material.

Alternatively, or additionally, the biochemically active component may be combined with or incorporated into an effective amount of a water soluble or insoluble matrix material to allow release, preferably a controlled rate of release, of the biochemically active component into the intervertebral disc, for example, over an extended period of time in which the patient requires treatment.

As noted elsewhere herein, one or more cyclodextrins may be combined with the biochemically active component and are effective in providing time controlled release of the biochemically active component from the implant element 220.

Preferably, the implant element 220 is substantially entirely comprised of substances that are sorbable, for example, absorbable or resorbable, into the body of the human or animal, for example, disc 14, such that after a sufficient period of time, the implant element 220 is entirely assimilated into the human or animal patient. In other words, in some embodiments of the invention, the implant element 220 advantageously provides no significant long term structural changes or structural alterations to the disc, surrounding spinal vertebrae or other structures.

The implant element 220 may be somewhat cylindrical in shape, with a diameter of no greater than about half of the height of the disc 14. Thus, implantation of the implant element 220 will cause no substantial change in a thickness of the disc, or no substantial separation of the adjacent vertebrae.

In one aspect of the invention, the system 210 may comprise a delivery device 230 that is structured to enable a physician or therapist to deliver a controlled dose of the implant element 220 to the patient. For example, the implant element 220 may be provided in the form of a gelatinous substance, for example, in cylindrical, ribbon or strand form, disposed in a lumen of catheter 236.

It is to be understood that the material or materials included within the present implant elements are to be such as to have no substantial or significant detrimental effect on the patient in general and on the intervertebral discs in particular.

Turning now to FIG. 4, another spinal disc therapy system in accordance with the present invention is generally shown at 310. The system 310 is substantially similar to systems 10, 110 and 210 shown in FIGS. 1, 2 and 3, respectively, with like elements having like reference numerals increased 300, 200 and 100, respectively. The system 310 comprises implant element 320 structured to be placed into, for example, substantially entirely within, the disc annulus 16, preferably between the fibrous lamellae 345. The implant element 320 is shown being introduced into the disc annulus 16 through a surgically made bore 346 having an opening at an outer wall of the annulus 16. The implant element 320 preferably is delivered from a posterior lateral approach into the bore 346 by means of a delivery device 330 structured to introduce the implant element 320, or at least a portion thereof, into the disc annulus 16, preferably such that the implant element 320 is implanted within a posterior wall 322 of the annulus.

FIG. 4*a* shows another spinal disc therapy system 410 of the invention, similar to the system 310 shown in FIG. 4, with a primary distinction being that the implant element 420 is specifically structured to be injected directly into the annulus 16 of the intervertebral disc 14, without an initial surgical bore being provided therein. The system 410 is substantially similar to system 310 shown in FIG. 4, with like elements having like reference numerals increased by 100.

In the aspect of the invention shown in FIG. 4*a*, the implant element 420 is in the form of a material that will conform to the internal structural elements of the intervertebral annulus, for example, by seeping between adjacent lamellae 345, and/or filling any spaces within damaged annulus tissue, at or in proximity to the site of injection.

The implant element 420 may comprise a fluid material, more preferably a gelatinous material, or gel, for example, a dissolvable, bioabsorbable gel, comprising, for example, encapsulated biochemically active agents in the form of a gelatinous strip or strand. The biochemically active agents may be those agents known to those in the art that are useful in repairing damaged tissue, for example, damaged annulus tissue, agents for relieving pain or the like. In one particular embodiment, the implant element 420 comprises lidocaine. Preferably, the implant element 420 is structured to allow release of the active agent over an extended period of time, for example, in a time controlled manner. It is to be appreciated that the implant element 320 or 420 may comprise a mechanically active or activatable component such as described elsewhere herein. For example, the implant element 320 or 420 may comprise an electrode filament.

Incorporated herein by this specific reference thereto is the entire disclosure of each of following United States patents: Brown et al., U.S. Pat. No. 4,393,041, Redl et al., U.S. Pat. No. 5,139,527, McGregor et al., U.S. Pat. No. 5,869,080, and Athanasiou et al., U.S. Pat. No. 6,013,853.

The present invention also provides methods for treating a human or an animal having an intervertebral disc.

In one embodiment of a method in accordance with the invention, the method generally comprises the steps of placing, into an intervertebral disc of a human or an animal, an implant element having a biochemically active substance and a excipient substance, for example, implant element 220, 320 or 420. Preferably, the implant element is introduced into the disc from a posterior lateral approach.

For example, biochemically active agent may comprise a medicinal substance effective in reducing at least one of inflammation and pain emanating from and/or in proximity to an intervertebral disc in which the implant element has been placed and the excipient component may comprise a matrix material. The method further comprises the step of allowing the biochemically active agent to be released into the intervertebral disc and, preferably the implant element to be substantially entirely adsorbed into the intervertebral disc in which the implant element has been placed. In a related embodiment of the method of the invention, the excipient component comprises an encapsulating agent.

In another embodiment of the method of the invention, the method comprises the step of placing an implant element into an intervertebral disc wherein the implant element includes at least one of a mechanically active, therapeutic component and a mechanically activatable, therapeutic component, such as implant element 20, 120, 320 or 420. For example, the implant element is structured to provide at least one of a magnetic field, an electrical field, and a radioactive field and the like and combinations thereof. The method preferably includes the step of providing wave energy into the body of the human or animal from the implant element. For example, the implant element may comprise an electrode, for example, an electrode filament.

In this embodiment of the invention, the method may further comprise the step of activating the therapeutic component after the step of placing in order to cause a therapeutic effect in, or in proximity to, the intervertebral disc in which the implant element has been placed. The step of activating may include the step of remotely activating the therapeutic component, for example, using a control unit, as discussed elsewhere herein.

In each of the methods of the invention, the step of placing may comprise placing the implant element into a nucleus of the intervertebral disc, or alternatively, into an annulus of the intervertebral disc, for example, between the fibrous rings thereof.

While this invention has been described with respect to various specific examples and embodiments, it is to be understood that the invention is not limited thereto and that it can be variously practiced within the scope of the following claims.

What is claimed is:

1. A method for treating a human or an animal having an intervertebral disc, the method comprising:
   placing, into an intervertebral disc of a human or an animal, an implant element including a biochemically active component and an excipient component, the implant element causes no change in a thickness of the intervertebral disc as a result of the presence of the implant element in the intervertebral disc; and
   allowing the biochemically active component to be released into the intervertebral disc.

2. The method of claim 1 wherein the allowing step provides the implant element to be substantially entirely absorbed into the human or animal into whom the implant element has been placed.

3. The method of claim 1 wherein the step of allowing provides the implant element to be substantially entirely absorbed into the intervertebral disc in which the implant element has been placed.

4. The method of claim 1 wherein the step of placing comprises placing the implant element into a nucleus of the intervertebral disc or into an annulus of the intervertebral disc.

5. The method of claim 1 wherein the implant element comprises a gel.

6. The method of claim 1 wherein the biochemically active component is effective in reducing at least one of inflammation and pain emanating in or in proximity to the intervertebral disc in which the implant element has been placed.

7. The method of claim 1 wherein the excipient component comprises a matrix material or an encapsulating agent.

8. The method of claim 1 wherein the excipient component comprises a cyclodextrin.

9. A method for treating a condition in a human or an animal having an intervertebral disc, the method comprising:

placing an implant element into an intervertebral disc of a human or animal, the implant element including at least one of a mechanically active therapeutic component and a mechanically activatable therapeutic component, the implant element being structured to provide at least one of a magnetic field, an electrical field, and a radioactive field; and, thereafter, maintaining the implant element in the intervertebral disc for at least about 1 day.

10. The method of claim 9 wherein the step of placing comprises placing the implant element into a nucleus of the intervertebral disc or into an annulus of the intervertebral disc.

11. The method of claim 9 wherein the maintaining step comprises maintaining the implant element in the intervertebral disc for at least about 1 week.

12. The method of claim 9 wherein the implant element is structured to provide a magnetic field.

13. The method of claim 9 wherein the implant element is structured to provide an electrical field.

14. The method of claim 9 wherein the implant element is structured to provide a radioactive field.

15. The method of claim 9 wherein the implant element comprises an electrode.

16. The method of claim 9 wherein the implant element causes no change in a thickness of the intervertebral disc as a result of the presence of the implant element in the intervertebral disc.

17. The method of claim 9 further comprising the step of activating the therapeutic component after the step of placing in order to cause a therapeutic effect in, or in proximity to, the intervertebral disc in which the implant element has been placed.

* * * * *